United States Patent

Yamamoto et al.

[11] Patent Number: 5,948,913
[45] Date of Patent: *Sep. 7, 1999

[54] HYDRATE FOR DRUG USE

[75] Inventors: Kenjiro Yamamoto; Akihiko Miyadera; Hiroaki Kitaoka, all of Tokyo, Japan

[73] Assignee: Daiichi Pharmaceutical Co., Ltd., Tokyo, Japan

[ * ] Notice: This patent is subject to a terminal disclaimer.

[21] Appl. No.: 08/836,583

[22] PCT Filed: Nov. 14, 1995

[86] PCT No.: PCT/JP95/02317

§ 371 Date: May 14, 1997

§ 102(e) Date: May 14, 1997

[87] PCT Pub. No.: WO96/15124

PCT Pub. Date: May 23, 1996

[30] Foreign Application Priority Data

Nov. 14, 1994 [JP] Japan .................................. 6-278204

[51] Int. Cl.$^6$ ........................ C07D 403/14; A61K 31/495
[52] U.S. Cl. ............................................ 544/370; 514/253

[58] Field of Search ............................................... 544/370

[56] References Cited

U.S. PATENT DOCUMENTS 5,681,954  10/1997  Yamamoto et al. ..................... 544/370

FOREIGN PATENT DOCUMENTS

| 624584 | 11/1994 | European Pat. Off. . | |
|---|---|---|---|
| 627219 | 12/1994 | European Pat. Off. . | |
| 7/41431 | 2/1995 | Japan | A61K 45/00 |
| 7-97364 | 4/1995 | Japan | C07D 7/325 |

*Primary Examiner*—Emily Bernhardt
*Attorney, Agent, or Firm*—Sughrue, Mion, Zinn, Macpeak & Seas, PLLC

[57] ABSTRACT

Crystals of 3-[2-[4-(3-chloro-2-methylphenyl)-1-piperazinyl]ethyl]-5,6-dimethoxy-1-(4-imidazolylmethyl)-1H-indazole dihydrochloride which is a hydrate for pharmaceutical use having excellent characteristics as a pharmaceutical material that has high storage stability and which substantially has specified X-ray diffraction characteristics, more particularly, the dihydrochloride is 3.5-hydrate.

2 Claims, 3 Drawing Sheets

HYDRATE FOR DRUG USE

TECHNICAL FIELD

This invention relates to dihydrochloride, which is also a water molecule-containing hydrate, of 3-[2-[4-(3-chloro-2-methylphenyl)-1-piperazinyl]ethyl]-5,6-dimethoxy-1-(4-imidazolylmethyl)-1H-indazole represented by formula (1):

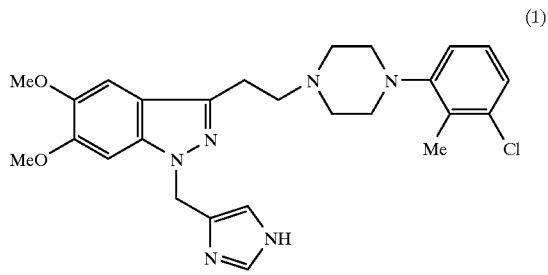

(1)

and to a production method thereof, and further relates to the use of the hydrate in the therapeutic treatment of human or animals or in the production of pharmaceutical preparations.

BACKGROUND ART

It has been disclosed, for example, in U.S. Pat. No. 3,362,956 that certain indazole derivatives are possessed of central nervous actions such as antianxietic activity, antiepileptic activity and the like. Also, there is a description in Arzneim.-Forsch., 37(4), 498–502 (1987), stating that certain piperazine derivatives have a function to inhibit calmodulin.

The compound represented by the formula (1) is a novel compound, and its salts and hydrates are also novel compounds. It was revealed that this compound represented by the formula (1) and its salts can show strong calmodulin inhibition action and also show excellent brain protecting action in various cerebral disorder animal models. In consequence, this compound is expected as a drug for use in the prevention and treatment of various diseases caused by the excess activation of calmodulin and cerebral disorders caused by ischemic brain disease, brain degenerative disease, traumatic brain disease, drug intoxication, hypoxia and the like.

Hydrochloride anhydrate of the compound of formula (1) can be prepared by carrying out crystal precipitation treatment of the free base from a mixture of an organic solvent and hydrochloric acid. However, it was found that crystals of the anhydrate obtained in this manner contain the organic solvent used for the crystal precipitation, and the solvent contained in the crystals cannot easily be removed even by heat drying under a reduced pressure. For example, when ethanol was used, the amount of ethanol contained in the crystals was a large and broad value of from 18,000 to 33,000 ppm. It was revealed also that prediction of the amount of solvent contained in the crystals and its regulation to a predetermined level cannot be made easily.

On the other hand, when methanol was used as the solvent at the time of crystal precipitation, the thus obtained hydrochloride anhydrate of the compound of formula (1) also contained methanol, but it was able to remove the contained methanol almost completely when the crystals were dried with heating (120° C.) under a reduced pressure for several days or more. However, the hydrochloride anhydrate obtained by removing methanol in this way showed a property to absorb moisture in response to the environmental humidity at room temperature (showed a property to absorb moisture when the humidity is high but release moisture when humidity is low, see FIG. 1).

Thus, it was revealed that crystals of the hydrochloride anhydrate of the compound of formula (1) cannot easily be made into pharmaceutical preparations, because they cause various problems, so that they are not appropriate as a pharmaceutical material.

DISCLOSURE OF THE INVENTION

The object of the present invention is to provide 3-[2-[4-(3-chloro-2-methylphenyl)-1-piperazinyl]ethyl]-5,6-dimethoxy-1-(4-imidazolylmethyl)-1H-indazole hydrochloride which is free from the aforementioned problems and has excellent characteristics as a pharmaceutical material having high storage stability. With the aim of achieving this object, the inventors of the present invention have conducted intensive studies.

As the result, it has been found to our surprise that a hydrate of 3-[2-[4-(3-chloro-2-methylphenyl)-1-piperazinyl]ethyl]-5,6-dimethoxy-1-(4-imidazolylmethyl)-1H-indazole hydrochloride does not have the disadvantages of its hydrochloride anhydrate and is completely stable when stored under general environmental conditions. This hydrate has a crystal form of 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate represented by formula (2):

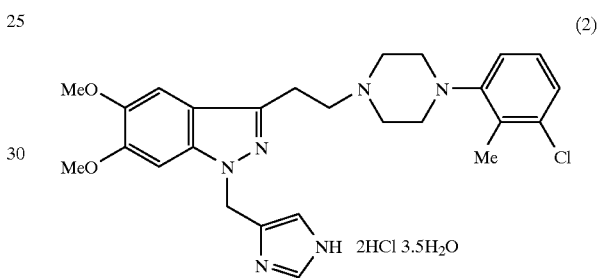

(2)

(sometimes to be referred simply as dihydrochloride 3.5-hydrate hereinafter).

Accordingly, the present invention relates to a crystal of 3-[2-[4-(3-chloro-2-methylphenyl)-1-piperazinyl]ethyl]-5,6-dimethoxy-1-(4-imidazolylmethyl)-1H-indazole dihydrochloride which substantially has the following X-ray diffraction characteristics.

| Lattice spacing d value (Å) | Relative strength |
|---|---|
| 28.1 | medium |
| 27.5 | medium |
| 27.0 | medium |
| 26.4 | medium |
| 25.6 | medium |
| 25.3 | strong |
| 24.7 | medium |
| 24.3 | strong |
| 22.0 | strong |
| 21.4 | weak |
| 20.9 | medium |
| 19.3 | extremely weak |
| 17.8 | medium |
| 15.4 | medium |
| 13.8 | medium |
| 9.60 | extremely strong |
| 9.09 | extremely weak |
| 8.46 | medium |

The present invention also relates to the aforementioned crystal in which the crystal of 3-[2-[4-(3-chloro-2-methylphenyl)-1-piperazinyl]ethyl]-5,6-dimethoxy-1-(4-imidazolylmethyl)-1H-indazole dihydrochloride is 3.5-hydrate.

The present invention also relates to a method for the production of 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate which comprises (a) treating free form 3-[2-[4-(3-chloro-2-methylphenyl)-1-piperazinyl]ethyl]-5,6-dimethoxy-1-(4-imidazolylmethyl)-1H-indazole with hydrochloric acid in the presence of water, or (b) treating a 3-[2-[4-(3-chloro-2-methylphenyl)-1-piperazinyl]ethyl]-5,6-dimethoxy-1-(4-imidazolylmethyl)-1H-indazole hydrochloride hydrate, which is a hydrate and/or hydrochloride less than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate, with water or/and hydrochloric acid, or (c) removing water and/or hydrochloric acid from a 3-[2-[4-(3-chloro-2-methylphenyl)-1-piperazinyl]ethyl]-5,6-dimethoxy-1-(4-imidazolylmethyl)-1H-indazole hydrochloride hydrate which is a hydrate and/or hydrochloride more than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate to be produced, or (d) treating a salt of 3-[2-[4-(3-chloro-2-methylphenyl)-1-piperazinyl]ethyl]-5,6-dimethoxy-1-(4-imidazolylmethyl)-1H-indazole other than hydrochloride with water and hydrochloric acid.

The present invention also relates to a method for the production of 3-[2-[4-(3-chloro-2-methylphenyl)-1-piperazinyl]ethyl]-5,6-dimethoxy-1-(4-imidazolylmethyl)-1H-indazole dihydrochloride substantially having the following X-ray diffraction characteristics.

| Lattice spacing d value (Å) | Relative strength |
|---|---|
| 28.1 | medium |
| 27.5 | medium |
| 27.0 | medium |
| 26.4 | medium |
| 25.6 | medium |
| 25.3 | strong |
| 24.7 | medium |
| 24.3 | strong |
| 22.0 | strong |
| 21.4 | weak |
| 20.9 | medium |
| 19.3 | extremely weak |
| 17.8 | medium |
| 15.4 | medium |
| 13.8 | medium |
| 9.60 | extremely strong |
| 9.09 | extremely weak |
| 8.46 | medium | which comprises (a) treating free form 3-[2-[4-(3-chloro-2-methylphenyl)-1-piperazinyl]ethyl]-5,6-dimethoxy-1-(4-imidazolylmethyl)-1H-indazole with hydrochloric acid in the presence of water, or (b) treating a 3-[2-[4-(3-chloro-2-methylphenyl)-1-piperazinyl]ethyl]-5,6-dimethoxy-1-(4-imidazolylmethyl)-1H-indazole hydrochloride hydrate, which is a hydrate and/or hydrochloride less than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate, with water or/and hydrochloric acid, or (c) removing water and/or hydrochloric acid from a 3-[2-[4-(3-chloro-2-methylphenyl)-1-piperazinyl] ethyl]-5,6-dimethoxy-1-(4-imidazolylmethyl)-1H-indazole hydrochloride hydrate which is a hydrate and/or hydrochloride more than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate to be produced, or (d) treating a salt of 3-[2-[4-(3-chloro-2-methylphenyl)-1-piperazinyl]ethyl]-5,6-dimethoxy-1-(4-imidazolylmethyl)-1H-indazole other than hydrochloride with water and hydrochloric acid.

The present invention also relates to the aforementioned production method in which the crystal of 3-[2-[4-(3-chloro-2-methylphenyl)-1-piperazinyl]ethyl]-5,6-dimethoxy-1-(4-imidazolylmethyl)-1H-indazole hydrochloride is 3.5-hydrate.

The present invention also relates to the aforementioned production method in which a free form of 3-[2-[4-(3-chloro-2-methylphenyl)-1-piperazinyl]ethyl]-5,6-dimethoxy-1-(4-imidazolylmethyl)-1H-indazole is treated with hydrochloric acid in the presence of water.

The present invention also relates to the aforementioned production method in which a 3-[2-[4-(3-chloro-2-methylphenyl)-1-piperazinyl]ethyl]-5,6-dimethoxy-1-(4-imidazolylmethyl)-1H-indazole hydrochloride hydrate, which is a hydrate and/or hydrochloride less than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate, is treated with water or/and hydrochloric acid.

The present invention also relates to the aforementioned production method in which water and/or hydrochloric acid is removed from a 3-[2-[4-(3-chloro-2-methylphenyl)-1-piperazinyl]ethyl]-5,6-dimethoxy-1-(4-imidazolylmethyl)-1H-indazole hydrochloride hydrate which is a hydrate and/or hydrochloride more than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate to be produced.

The present invention also relates to the aforementioned production method in which a salt of 3-[2-[4-(3-chloro-2-methylphenyl)-1-piperazinyl]ethyl]-5,6-dimethoxy-1-(4-imidazolylmethyl)-1H-indazole other than hydrochloride is treated in the presence of water and hydrochloric acid.

On the other hand, the present invention also relates to 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate;

the aforementioned compound which is used in the therapeutic treatment of animals or human;

the aforementioned compound which is used in the treatment of diseases caused by excess expression of calmodulin;

the aforementioned compound or aforementioned crystal which is used in the treatment of brain diseases;

use of the aforementioned compound or aforementioned crystal in the formulation of pharmaceutical preparations;

use of the aforementioned compound or aforementioned crystal in the production of pharmaceutical preparations which are used for the treatment of brain diseases;

a pharmaceutical preparation which contains 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate and at least one pharmaceutically acceptable carrier;

a pharmaceutical preparation which contains crystals of 3-[2-[4-(3-chloro-2-methylphenyl)-1-piperazinyl]

ethyl]-5,6-dimethoxy-1-(4-imidazolylmethyl)-1H-indazole dihydrochloride substantially having the following X-ray diffraction characteristics.

| Lattice spacing d value (Å) | Relative strength |
|---|---|
| 28.1 | medium |
| 27.5 | medium |
| 27.0 | medium |
| 26.4 | medium |
| 25.6 | medium |
| 25.3 | strong |
| 24.7 | medium |
| 24.3 | strong |
| 22.0 | strong |
| 21.4 | weak |
| 20.9 | medium |
| 19.3 | extremely weak |
| 17.8 | medium |
| 15.4 | medium |
| 13.8 | medium |
| 9.60 | extremely strong |
| 9.09 | extremely weak |
| 8.46 | medium | and at least one pharmaceutically acceptable carrier;

the aforementioned pharmaceutical preparation in which the crystal of 3-[2-[4-(3-chloro-2-methylphenyl)-1-piperazinyl]ethyl]-5,6-dimethoxy-1-(4-imidazolylmethyl)-1H-indazole dihydrochloride is 3.5-hydrate;

the aforementioned pharmaceutical preparation in which the preparation is used for the treatment of diseases caused by the excess expression of calmodulin; and the aforementioned pharmaceutical preparation in which the preparation is used for the treatment of brain diseases.

The following describes the present invention in detail.

It has been found to our surprise that the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate of the present invention represented by the formula (2) has the following properties. That is, the hydrate did not show changes in its powder X-ray diffraction pattern or detectable water content when relative humidity was changed within the range of from about 20% to about 80% at 25° C. (FIG. 2). Also, changes in its appearance were hardly found and its changes in the content (determination by HPLC) were not found under dry heating conditions (50° C., tightly sealed in a bottle, 1 month) or wet heating conditions (40° C., 75% humidity, 1 month).

It is evident from these results that the dihydrochloride 3.5-hydrate (represented by the formula (2)) of the compound of formula (1) is possessed of excellent storage stability. It means therefore that this hydrate can be stored for a prolonged period of time without changes. Particularly, this hydrate does not absorb water molecules other than those which are contained as 3.5-hydrate, so that the amount of active ingredient contained as a pharmaceutical drug does not change during storage. In addition, it was found that it does not contain organic solvent in its crystals similar to the case of anhydrate.

Crystals of the dihydrochloride 3.5-hydrate of formula (2) can be characterized by its powder X-ray diffraction pattern, for example, they show the spectrum of FIG. 3 and its characteristic peaks of Table 6.

The dihydrochloride 3.5-hydrate of formula (2) is further characterized by its elemental analysis which coincided with the theoretical value of its molecular formula $C_{26}H_{31}ClN_6O_2 \cdot 2HCl \cdot 3.5H_2O$ (molecular weight: 631.00).

Calcd.; C, 49.49%; H, 6.39%; N, 13.32%; Cl, 16.86%; Found; C, 49.22%; H, 6.38%; N, 13.09%; Cl, 16.85%

The water content of the dihydrochloride.3.5-hydrate of formula (2) coincided with its theoretical value when measured by the Karl Fischer's method.

Calcd.: 9.99%; Found: 10.53%

The dihydrochloride 3.5-hydrate of formula (2) is also characterized by the thermal analysis of FIG. 4.

The dihydrochloride 3.5-hydrate of formula (2) can be prepared by a method selected from the following methods.

(a) A method in which free form 3-[2-[4-(3-chloro-2-methylphenyl)-1-piperazinyl]ethyl]-5,6-dimethoxy-1-(4-imidazolylmethyl)-1H-indazole is treated with hydrochloric acid in the presence of water.

(b) A method in which a 3-[2-[4-(3-chloro-2-methylphenyl)-1-piperazinyl]ethyl]-5,6-dimethoxy-1-(4-imidazolylmethyl)-1H-indazole hydrochloride hydrate, which is a hydrate and/or hydrochloride less than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate to be produced, is treated with water or/and hydrochloric acid.

(c) A method in which water and/or hydrochloric acid is removed from a 3-[2-[4-(3-chloro-2-methylphenyl)-1-piperazinyl]ethyl]-5,6-dimethoxy-1-(4-imidazolylmethyl)-1H-indazole hydrochloride hydrate, which is a hydrate and/or hydrochloride more than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate to be produced, for example, by neutralization, drying and the like means.

(d) A method in which a salt of 3-[2-[4-(3-chloro-2-methylphenyl)-1-piperazinyl]ethyl]-5,6-dimethoxy-1-(4-imidazolylmethyl)-1H-indazole other than hydrochloride is treated in the presence of water and hydrochloric acid. In this case, as occasion demands, the treatment may be carried out after obtaining the free form compound.

In carrying out the aforementioned treatment, organic solvents may be used as occasion demands. It is most general to use alcohols as such solvents, and, when toxicity is taken into consideration, ethanol or propanol is desirable and ethanol is more desirable.

To carry out the treatment means to allow the material compound to react with hydrochloric acid in the presence of water, in order to effect formation of crystals of the intended hydrochloride hydrate. This can be carried out under a state of suspension, but it is desirable in general to carry out the treatment under a state of solution. In that case, a purification step may be employed, for example, by adding activated carbon.

When a hydrochloride containing more hydrochloric acid than the case of dihydrochloride or an acid addition salt other than hydrochloride is neutralized, it may be neutralized by allowing it to react with a hydroxide, carbonate, bicarbonate, alkoxide or the like of an alkali metal in a solution. Thereafter, the free form compound can be obtained by a usually used method, if necessary, carrying out extraction and the like treatments.

In the case of crystals containing excess hydrochloric acid (hydrogen chloride) or water, it may be effective in some cases depending on their properties to once obtain the free form and then convert it into the compound of interest, rather than obtaining the crystals of interest by neutralization, drying and the like means.

When the free form or crystals containing less hydrochloric acid are converted into dihydrochloride, hydrochloric acid may be used in an amount within the range of from the same equivalent to 3 equivalents, generally within the range of from 1.5 to 2 equivalents. The amount of water to be used is approximately from 2 to 20 times than the weight of crystals to be used, preferably within the range of from 3 to 5 times. (When 2 ml of water is used for 1 g of crude crystals, it means 2 times.)

Preferred method for the production of the dihydrochloride 3.5-hydrate is a method in which appropriate amounts of 1 N hydrochloric acid and water are added to the free form compound of formula (I), the mixture is dissolved by heating and the thus obtained uniform solution is then cooled to room temperature while stirring, thereby effecting crystallization of the intended compound.

The dihydrochloride 3.5-hydrate of the present invention exerts its effects not only by its oral administration but also by its parenteral administration, particularly intravenous injection, because of its solubility in water. In consequence, it can be administered by both oral and parenteral methods.

Dosage of the dihydrochloride 3.5-hydrate of the present invention can be optionally changed depending on the symptoms, age, weight and the like of each patient. In general, its dose for oral administration may be within the range of from 1 mg to 1,000 mg, preferably from 10 mg to 500 mg, per day per adult. Examples of its dosage form include tablets, capsules, powders, granules and the like. These can be produced by known formulation techniques, together with usual fillers, lubricants, binders and the like additive agents. In the case of parenteral administration, the dose may be within the range of from 1 mg to 500 mg, preferably from 10 mg to 250 mg, per day per adult, which may be administered by subcutaneous or intravenous injection or drip infusion.

A pharmaceutical preparation which contains the dihydrochloride.3.5-hydrate of the present invention represented by the formula (2), when used in combination with other drugs, will exert additional and synergistic effects on the prevention and treatment of various diseases. Examples of such drugs include a cerebral circulation ameliorater (cinepazide maleate or the like), a cerebral metabolism ameliorater (idebenone, indeloxazine or the like), a antipsychotic agent (timiperone or the like, imiplamin or the like, diazepam or the like), an intracranial decompression agent (glyceol or the like), an antihypertensive drug, a vasodilator drug (trapidil or the like), an antipyretic-analgesic-antiphlogistic drug, an anti-inflammatory steroid, an anti-platelet agent (ticlopidine or the like), an anticoagulant (heparin or the like), a fibrinolysis inducing agent (tissue plasminogen activator or the like), a diuretic, an antilipidemic agent (probucol or the like), an antiulcer drug, an artificial blood preparation, a hepatic disease treating agent, an anti-malignant tumor drug and the like.

PREPARATION EXAMPLES

The dihydrochloride 3.5-hydrate of the present invention can be made into pharmaceutical preparations by generally known methods. These methods are illustratively described with reference to the following formulation examples, though the present invention is not restricted by these examples as a matter of course. Prescriptions in which the compound prepared in Inventive Example 3 was used was employed in the formulation examples.

PREPARATION EXAMPLE 1

| (1) | Compound of Inventive Example 3 | 10 g |
|---|---|---|
| (2) | Lactose | 50 g |
| (3) | Corn starch | 15 g |
| (4) | Hydroxypropylcellulose | 8 g |
| (5) | Carboxymethylstarch sodium | 7 g |
| (6) | Magnesium stearate | 1 g |

The above components (1), (2), (3) and (5) are put into a fluidized bed granulating machine and uniformly mixed, and the mixture is made into granules using 6% aqueous solution of the component (4) as a binding solution. This is mixed uniformly with the component (6) and used as a mixture powder for tablet making use. Using this, 100 tablets each having a diameter of 8 mm and containing 100 mg of (1) are prepared.

PREPARATION EXAMPLE 2

| (1) | Compound of Inventive Example 3 | 2 g |
|---|---|---|
| (2) | 0.1N Hydrochloric acid | 150 ml |
| (3) | Glucose | 50 g |
| (4) | Distilled water for injection use | balance (see the following) |

The above components (1) (2) and (3) are mixed and solubilized and then adjusted to a total volume of 1,000 ml by adding distilled water for injection use. This solution is subjected to sterile filtration using a 0.2 μm filter and then distributed in 10 ml portions into 10 ml capacity ampuls.

BEST MODE OF CARRYING OUT THE INVENTION

Figure 1:
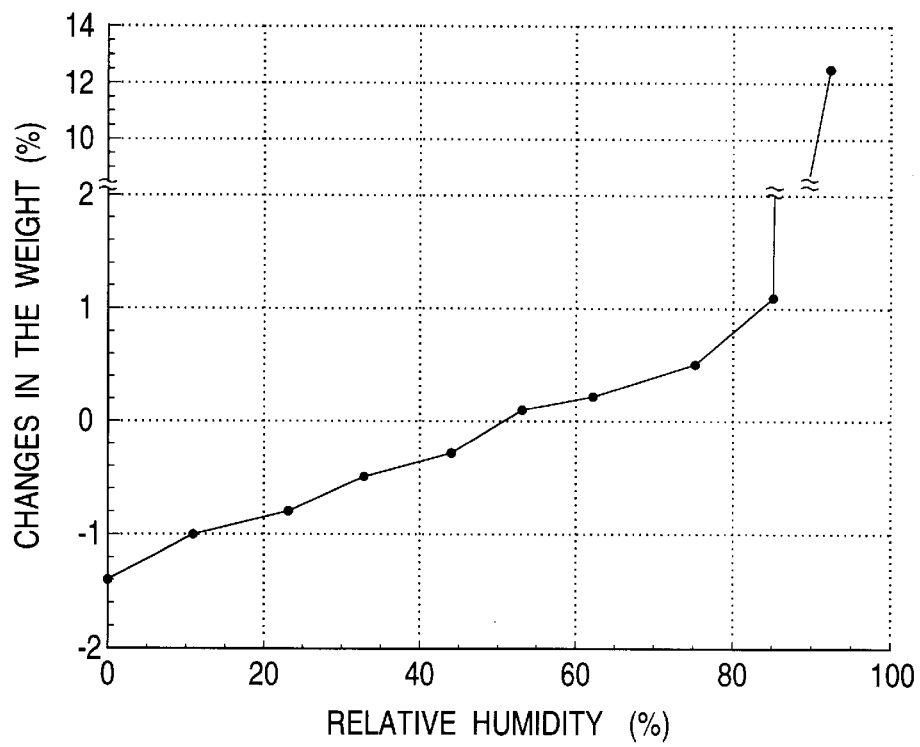
FIG. 1 is a graph showing changes in the weight of 3-[2-[4-(3-chloro-2-methylphenyl)-1-piperazinyl]ethyl]-5,6-dimethoxy-1-(4-imidazolylmethyl)-1H-indazole hydrochloride anhydrate plotted as a function of humidity.
Figure 2:
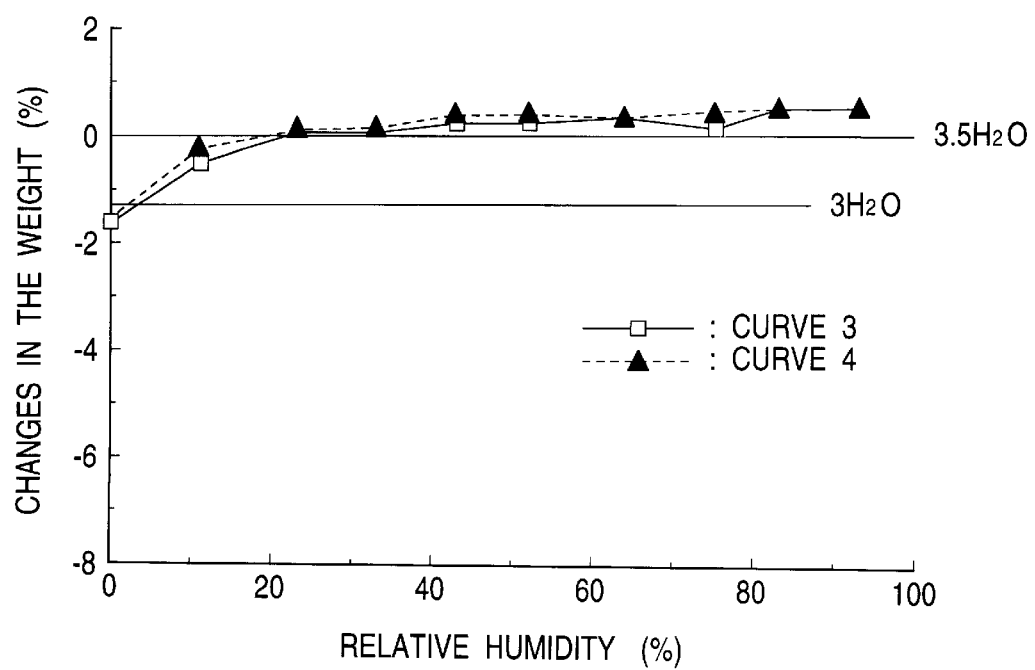
FIG. 2 is a graph showing changes in the weight of the 3.5-hydrate of the present invention plotted as a function of humidity.
Figure 3:
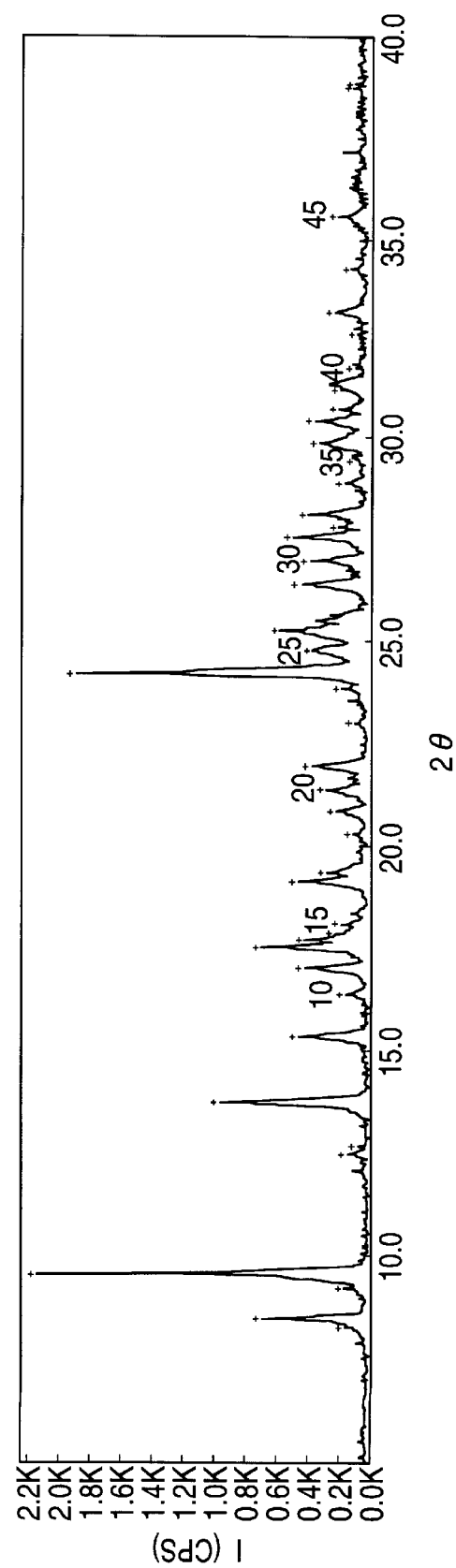
FIG. 3 is a powder X-ray diffraction spectrum of the 3.5-hydrate of the present invention.
Figure 4:
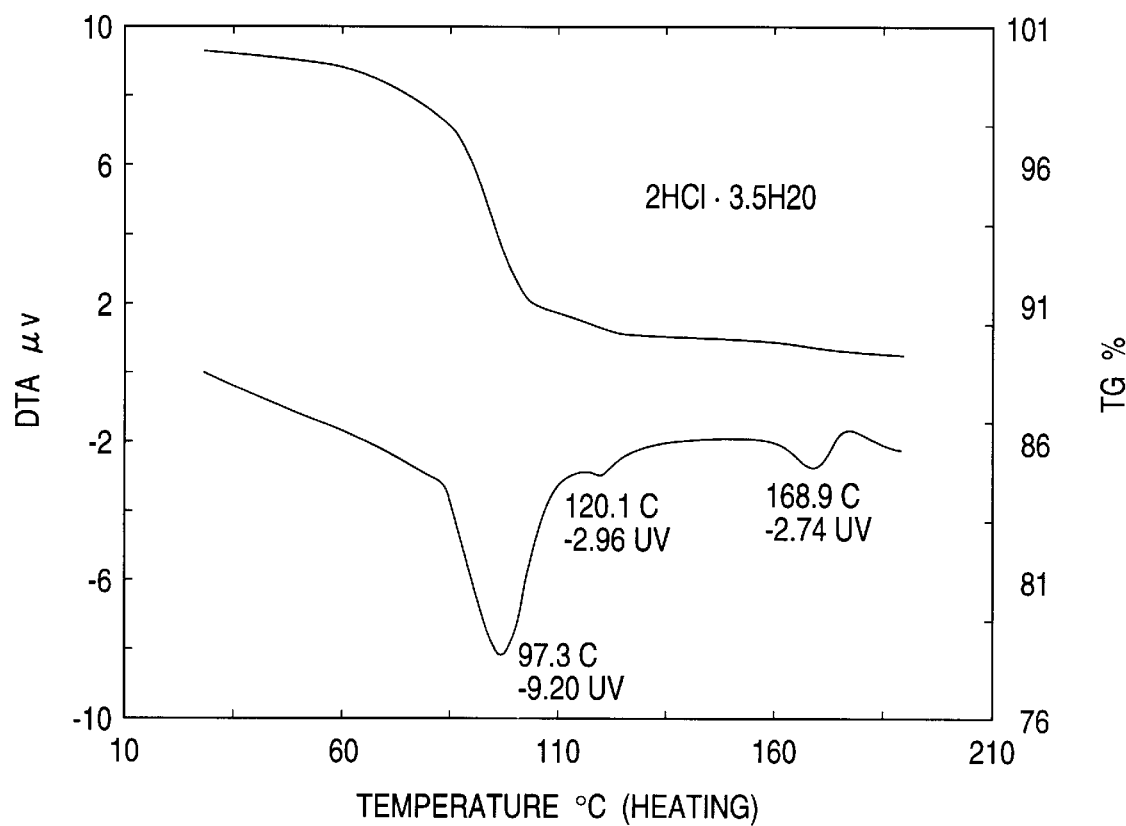
FIG. 4 is a thermal analysis spectrum of the 3.5-hydrate of the present invention.

The present invention is described further in detail with reference to the following examples, though the invention is not restricted thereby as a matter of course.

REFERENCE EXAMPLE 1

Ethyl 5,6-dimethoxy-1-(1-trityl-4-imidazolyl) methyl-1H-indazole-3-carboxylate

Ethyl 5,6-dimethoxyindazole-3-carboxylate (250.2 g) was suspended in dimethyl sulfoxide (5,000 ml), and the suspension was mixed with lithium methoxide (40.2 g) and stirred at room temperature. After 1 hour of stirring at room temperature, to this was added dropwise dimethyl sulfoxide (2,000 ml) solution of 4-chloromethyl-1-tritylimidazole (447.8 g) at room temperature spending 10 minutes. When the resulting mixture was stirred as such at room temperature for 2 hours, mixed with lithium methoxide (4.2 g) and 4-chloromethyl-1-tritylimidazole (44.8 g) and then stirred at room temperature for 1 hour, it was observed that the spot of the material almost disappeared on a thin layer chromatography (chloroform/ethanol=30/1). When the reaction solution was poured into ice water (30,000 ml) which was stirred, crystals were precipitated. The crystals were collected by suction filtration, washed with water (2,000 ml×3) and then air-dried. They were dissolved in chloroform (10,000 ml), the resulting solution was dried with sodium sulfate and filtered and then the solvent was evaporated under a reduced pressure. The resulting residue was separated and purified by a silica gel column (chloroform/ethanol=50/1) and recrystallized from chloroform-isopropyl alcohol to obtain 222.0 g of colorless prism crystals (melting point: 184–186° C.).

IR (KBr) cm$^{-1}$: 1704, 1496, 1268, 1146, 1132, 1092, 748, 700 $^1$H-NMR δ (ppm, CDCl$_3$): 1.21 (6 H, d, J=5.9 Hz, Me of iso-PrOH), 1.46 (3 H, t, J=7.3 Hz), 3.93 (3 H, s), 3.97 (3 H, s), 4.01 (1 H, m, CH of iso-PrOH), 4.49 (2 H, q, J=7.3 Hz), 5.61 (2 H, s), 6.79 (1 H, s), 7.03 (5 H, m), (7.13 (1 H, s), 7.28 (10 H, m), 7.47 (1 H, s), 7.51 (1 H, s). Elemental analysis for C$_{35}$H$_{32}$N$_4$O$_4$.C$_3$H$_8$O Calcd.; C 72.13%; H 6.37%; N 8.85%; Found; C 71.53%; H 6.37%; N 8.70%

REFERENCE EXAMPLE 2

5,6-Dimethoxy-1-(1-trityl-4-imidazolyl)methyl-1H-indazole-3-methanol

Ethyl 5,6-dimethoxy-1-(1-trityl-4-imidazolyl)methyl-1H-indazole-3-carboxylate (222.0 g) was ground into a powder form using a mortar and suspended in tetrahydrofuran (1,300 ml) at room temperature, and the suspension was cooled with ice water. To this was added sodium bis-methoxyethoxyaluminum hydride (3.4 M toluene solution, about 250.0 ml) spending 15 minutes, subsequently stirring in an ice bath. It was observed 30 minutes thereafter that the spot of the material almost disappeared on a thin layer chromatography (ethyl acetate/hexane=2/1). The reaction solution was mixed with super-saturated sodium sulfate aqueous solution, stirred for 1 hour, mixed with sodium sulfate and then filtered. In this case, sodium sulfate on the filter was washed with hot chloroform (500 ml×5). The filtrate and washed solution were combined and the solvent was evaporated under a reduced pressure to obtain colorless solid (220.1 g). This was recrystallized from chloroform to obtain 181.0 g of colorless prism crystals (melting point: 115–120° C. (dec.)).

IR (KBr) cm$^{-1}$: 3216, 3172, 3008, 2936, 1510, 1488, 1472, 1444, 1302, 1260, 1172, 1156, 1128, 1102, 1036, 1014, 836, 764, 746, 702, 678, 666, 636 $^1$H-NMR δ (ppm, CDCl$_3$): 3.91 (3 H, s), 3.92 (3 H, s), 4.92 (2 H, s), 5.44 (2 H, s), 6.76 (1 H, s), 6.95 (1 H, s), 7.05 (5 H, m), 7.26 (1 H, s, CHCl$_3$), 7.28 (1 H, s), 7.31 (10 H, m), 7.46 (1 H, s) Elemental analysis for C$_{33}$H$_{30}$N$_4$O$_3$.CHCl$_3$ Calcd.; C 62.83%; H 4.81%; N 8.62%; Found; C 62.50%; H 4.63%; N 8.42%

REFERENCE EXAMPLE 3

3-Chloromethyl-5,6-dimethoxy-1-(1-trityl-4-imidazolyl)methyl-1H-indazole 5,6-Dimethoxy-1-(1-trityl-4-imidazolyl)methyl-1H-indazole-3-methanol (180.0 g) was ground into a powder form using a mortar and suspended in dichloromethane (1,700 ml) at room temperature. After suspension, the reaction solution was stirred with cooling in an ice bath. To this was added dropwise 48.6 ml of thionyl chloride spending 5 minutes. It was observed 1 minute thereafter that the spot of the material almost disappeared on a thin layer chromatography (chloroform/ethanol=30/1). The reaction solution was poured into saturated sodium bicarbonate aqueous solution (2,000 ml) and extracted with chloroform (5,000 ml), and the extract was dried with sodium sulfate, filtered and then evaporated under a reduced pressure to obtain colorless solid (165.1 g). This solid substance was used in the subsequent reaction as such.

$^1$H-NMR δ (ppm, CDCl$_3$):
3.95 (3 H, s), 4.09 (3 H, s), 4.83 (2 H, s), 5.67 (2 H, s), 7.02 (8 H, m), 7.37 (10 H, m), 7.88 (1 H, br)

REFERENCE EXAMPLE 4

5,6-Dimethoxy-1-(1-trityl-4-imidazolyl)methyl-1H-indazole-3-acetonitrile

3-Chloromethyl-5,6-dimethoxy-1-(1-trityl-4-imidazolyl)methyl-1H-indazole (165.0 g) was suspended in dimethyl sulfoxide (1,200 ml) and stirred at room temperature. To this was added potassium cyanate (43.6 g) which has been made into powder using a mortar. When the reaction solution was stirred at 70° C. for 1 hour, the reaction solution became uniform and transparent, and it was observed that the spot of the material almost disappeared on a thin layer chromatography (ethyl acetate/hexane=2/1). The reaction solution was cooled to room temperature and poured into water (15,000 ml) which was vigorously stirred, and the mixture was stirred for 1 hour. The thus precipitated solid substance was collected by suction filtration, washed with water (1,000 ml×3) and dissolved in chloroform (5,000 ml), the resulting solution was dried with sodium sulfate and filtered, and then the solvent was evaporated under a reduced pressure. The thus obtained residue was separated and purified by a silica gel column (ethyl acetate) to obtain 108.7 g of light brown solid. This solid substance was directly used in the subsequent reaction.

$^1$H-NMR δ (ppm, CDCl$_3$): 3.92 (3 H, s), 3.94 (3 H, s), 3.97 (2 H, s), 5.42 (2 H, s), 6.79 (1 H, s), 7.00 (1 H, s), 7.02 (1 H, s), 7.06 (5 H, m), 7.30 (10 H, m), 7.46 (1 H, s)

REFERENCE EXAMPLE 5

5,6-Dimethoxy-1-(1-trityl-4-imidazolyl)methyl-1H-indazole-3-acetic acid 5,6-Dimethoxy-1-(1-trityl-4-imidazolyl)methyl-1H-indazole-3-acetonitrile (107.0 g) was suspended in ethanol (1,000 ml) at room temperature. To this was added 10 N sodium hydroxide aqueous solution (40.0 g sodium hydroxide, prepared from 100 ml of water), subsequently heating the mixture under reflux. It was observed 6 hours thereafter that the spot of the material almost disappeared on a thin layer chromatography (ethyl acetate). The reaction solution was cooled to room temperature and poured into water (5,000 ml). When this was adjusted to pH 3 to 4 with 10% hydrochloric acid aqueous solution, a colorless solid substance was precipitated. This was collected by filtration and washed with water (500 ml×3). The thus obtained solid substance was dissolved in chloroform (5,000 ml), the resulting solution was dried with sodium sulfate and filtered and then the solvent was evaporated under a reduced pressure. The thus obtained 134.0 g of solid substance was directly used in the subsequent reaction.

$^1$H-NMR δ (ppm, CDCl$_3$): 3.84 (3 H, s), 3.87 (3 H, s), 3.89 (2 H, s), 5.43 (2 H, s), 6.76 (1 H, s), 6.88 (1 H, s), 6.93 (1 H, s), 7.03 (5 H, m), 7.28 (10 H, m), 7.48 (1 H, s)

REFERENCE EXAMPLE 6

4-(3-Chloro-2-methylphenyl)-1-[[5,6-dimethoxy-1-(-trityl-4-imidazolyl)methyl-1H-indazol-3-yl]acetyl] piperazine 5,6-Dimethoxy-1-(1-trityl-4-imidazolyl)methyl-1H-indazole-3-acetic acid (134.0 g) was suspended in dichloromethane (1,000 ml). To this were added 2,2-dipyridyl disulfide (63.5 g) and triphenylphosphine (75.6 g), subsequently stirring the mixture at room temperature (the suspension became uniform solution). To this was added dropwise dichloromethane (200 ml) solution of 4-(3-chloro-2-methylphenyl)piperazine (60.7 g) spending 5 minutes, followed by 5 hours of stirring at room temperature. It was observed that the spot of the material almost disappeared on a thin layer chromatography (ethyl acetate/hexane=3/1). Dichloromethane in the reaction solution was evaporated under a reduced pressure, and the thus obtained residue was mixed with hot ethyl acetate and stirred to find precipitation of a solid substance. This was collected by suction filtration, washed with ethyl acetate (500 ml×2) and then air-dried to obtain 140.4 g of a colorless solid substance. The solid substance was separated and purified by a silica gel column (chloroform/ethanol=30/1) to obtain 134.9 g of colorless solid. This was recrystallized from ethanol to obtain 120.0 g of colorless prism crystals (m.p. 103–105° C.).

IR (KBr) cm$^{-1}$: 1646, 1628, 1508, 1466, 1450, 1430, 1260, 750, 702 $^1$H-NMR δ (ppm, CDCl$_3$): 1.23 (1.2 H, t, J=6.8 Hz), Me of EtOH), 2.28 (3 H, s), 2.55 (2 H, m), 2.73 (2 H, m), 3.67 (4 H, m), 3.71 (0.8 H, q, J=6.8 Hz, CH$_2$ of EtOH), 3.90 (3 H, s), 3.93 (3 H, s), 4.03 (2 H, s), 5.43 (2 H, s), 6.68 (1 H, s), 6.72 (1 H, d, J=8.3 Hz), 6.90 (1 H, s), 7.03 (7 H, m), 7.14 (1 H, s), 7.27 (10 H, m), 7.41 (1 H, s) Elemental analysis for C$_{45}$H$_{43}$N$_6$O$_3$Cl.0.4EtOH.H$_2$O Calcd.; C 70.10%; H 5.70%; N 10.70%; Cl 4.72%; Found; C 70.02%; H 5.78%; N 10.60%; Cl 5.11

INVENTIVE EXAMPLE 1

3-[2-[4-(3-Chloro-2-methylphenyl)-1-piperazinyl] ethyl]-5,6-dimethoxy-1-(4-imidazolylmethyl)-1H-indazole 4-(3-Chloro-2-methylphenyl)-1-[[[5,6-dimethoxy-1-(1-trityl-4-imidazolyl)methyl]indazol-3-yl]acetyl]piperazine (120.0 g) was suspended in tetrahydrofuran (1,000 ml). To this was added 1.0 M borane tetrahydrofuran complex (800 ml), subsequently heating the mixture under reflux. It was observed 90 minutes thereafter that the spot of the material almost disappeared on a thin layer chromatography (ethyl acetate). The reaction solution was cooled to room temperature and mixed with water (30 ml) to decompose excess reagent. After evaporation of tetrahydrofuran under a reduced pressure, the thus obtained residue was mixed with concentrated hydrochloric acid (150 ml), water (200 ml) and ethanol (40 ml) and stirred at 50° C. for 1 hour. The water layer was cooled to room temperature, alkalified with potassium carbonate and extracted with chloroform (3,000 ml), and the organic layer was dried with sodium sulfate and filtered, subsequently evaporating the solvent under a reduced pressure. The thus obtained residue was separated and purified by a silica gel column chromatography (chloroform/ethanol=40/1) to obtain a colorless solid. This was recrystallized from isopropyl alcohol-isopropyl ether to obtain 71.0 g of colorless prism crystals (melting point: 143–144.5° C.).

IR (KBr) cm$^{-1}$: 1510, 1464, 1432, 1272, 1238, 1206, 1006 $^1$H-NMR δ (ppm, CDCl$_3$): 2.34 (3 H, s), 2.78 (4 H, m), 2.90 (2 H, m), 2.97 (4 H, m), 3.17 (2 H, m), 3.90 (3 H, s), 3.91 (3 H, s), 5.45 (2 H, s), 6.83 (1 H, s), 6.84 (1 H, s), 6.92 (1 H, m), 7.00 (1 H, s), 7.09 (2 H, m), 7.52 (1 H, s) Elemental analysis for C$_{26}$H$_{31}$N$_6$O$_2$Cl Calcd.; C 63.09%; H 6.31%; N 16.98%; Cl 7.16%; Found ; C 62.93%; H 6.30%; N 16.88%; Cl 7.16%

INVENTIVE EXAMPLE 2

3-[2-[4-(3-Chloro-2-methylphenyl)-1-piperazinyl] ethyl]-5,6-dimethoxy-1-(4-imidazolylmethyl)-1H-indazole 1.5-hydrochloride (anhydrous crystals)

A 60 g portion of crystals of 3-[2-[4-(3-chloro-2-methylphenyl)-1-piperazinyl]ethyl]-5,6-dimethoxy-1-(4-imidazolylmethyl)-1H-indazole (free form) was dissolved in 1,000 ml of ethanol with heating. The resulting solution was mixed with 182.2 ml of 1 N hydrochloric acid and stirred for 20 minutes and then the solvent was evaporated under a reduced pressure. The thus obtained residue was dried at room temperature for 12 hours under a reduced pressure in the presence of phosphorus pentaoxide. The thus obtained powder was dissolved in 1,300 ml of anhydrous ethanol with heating. After the dissolution, the solution was concentrated to about 1,000 ml by heating. The thus concentrated solution was spontaneously cooled while stirring and, after adding seed crystals, further cooled spontaneously to room temperature while stirring. The thus precipitated crystals were collected by filtration and dried by heating (60° C.) for about 12 hours under a reduced pressure in the presence of phosphorus pentaoxide to obtain 64 g of colorless crystals (melting point: 226.5–228° C.).

IR (KBr) cm$^{-1}$: 2968, 2836, 2712, 2544, 2456, 1512, 1470, 1436, 1338, 1260, 1208, 1166, 1108, 1032, 1006, 862 $^1$H-NMR (ppm, d$_6$-DMSO) δ: 2.32 (3 H, s), 3.20–3.21 (3.5 H, m), 3.40–3.52 (10 H, m), 3.82, 3.86 (each 3 H, s), 5.53 (2 H, s), 7.08 (1 H, dd), 7.19–7.25 (2 H, m), 7.31–7.33 (3 H, m), 8.36 (1 H, s).

It was confirmed by an HPLC analysis that the crystals obtained in this case contained about 15,000 ppm of residual ethanol.

INVENTIVE EXAMPLE 3

3-[2-[4-(3-Chloro-2-methylphenyl)-1-piperazinyl] ethyl]-5,6-dimethoxy-1-(4-imidazolylmethyl)-1H-indazole dihydrochloride 3.5-hydrate A 4.95 g portion of free form 3-[2-[4-(3-chloro-2-methylphenyl)-1-piperazinyl]ethyl]-5,6-dimethoxy-1-(4-imidazolylmethyl)-1H-indazole was mixed with 20 ml of 1 N hydrochloric acid and distilled water to a total volume of 49.5 ml. Next, the reaction vessel was heated at an outside temperature of 120° C. to effect reflux inside the system, thereby completely dissolving the crystals. The thus dissolved solution was cooled to room temperature while stirring with a stirrer and then stirred for a whole day and night. The thus precipitated crystals were collected by filtration and air-dried for 2 days to obtain 5.5 g of colorless prism crystals (melting point: 166–167° C.).

IR (KBr) cm$^{-1}$: 3400, 2850, 1625, 1505, 1460, 1425, 1245, 1150, 1010, 840 $^1$H-NMR (ppm, d$_6$-DMSO) δ: 2.39 (3 H, s), 3.30–3.80 (20 H, m), 5.74 (2 H, s), 7.15 (1 H, dd), 7.28 (1 H, s), 7.30 (1 H, dd), 7.43 (1 H, s), 7.52 (1 H, s), 7.69 (1 H, s), 9.13 (1 H, s), 11.80 (1 H, bs), 14.80 (1 H, bs). Elemental analysis for C$_{26}$H$_{31}$N$_6$O$_2$Cl.2HCl.3.5H$_2$O Calcd.; C, 49.41; H, 6.54; N, 13.30; Cl, 16.83; Found; C, 49.15; H, 6.44; N, 13.29; Cl, 16.99.

| Powder X-ray diffraction data Measuring conditions; | |
|---|---|
| Ray source: | Cu—Kα ray (detector side, monochromatic ray by monochrometer) |
| Detector: | scintillation counter |
| X-ray voltage: 35 kV | Current: 20 mA |
| Scanning rate: 2°/min | Sampling space: 0.010° |
| Slit system: | |
| Divergence slit = 1.0° | Scattering slit = 1.0° |
| Receiving slit = 0.15 mm | |
| Apparatus: | Powder X-ray Diffractometer MXP-3V manufactured by Mack Science |

Characteristic peaks of the X-ray diffraction spectrum are shown in Table 6.

| Lattice spacing d value (Å) | Relative strength |
|---|---|
| 28.1 | medium |
| 27.5 | medium |
| 27.0 | medium |
| 26.4 | medium |
| 25.6 | medium |
| 25.3 | strong |
| 24.7 | medium |
| 24.3 | strong |
| 22.0 | strong |
| 21.4 | weak |
| 20.9 | medium |
| 19.3 | extremely weak |
| 17.8 | medium |
| 15.4 | medium |
| 13.8 | medium |
| 9.60 | extremely strong |
| 9.09 | extremely weak |
| 8.46 | medium |

INVENTIVE EXAMPLE 4

3-[2-[4-(3-Chloro-2-methylphenyl)-1-piperazinyl]ethyl]-5,6-dimethoxy-1-(4-imidazolylmethyl)-1H-indazole dihydrochloride 3.5-hydrate A 5.50 g portion of crystals of 3-[2-[4-(3-chloro-2-methylphenyl)-1-piperazinyl]ethyl]-5,6-dimethoxy-1-(4-imidazolylmethyl)-1H-indazole 1.5-hydrochloride (anhydrate) was mixed with 5.0 ml of 1 N hydrochloric acid and distilled water to a total volume of 49.5 ml. Next, the reaction vessel was heated at an outside temperature of 120° C. to effect reflux inside the system, thereby completely dissolving the crystals. The thus dissolved solution was cooled to room temperature while stirring with a stirrer and then stirred for a whole day and night. The thus precipitated crystals were collected by filtration and air-dried for 2 days to obtain 5.6 g. of colorless prism crystals (melting point: 166–167° C.).

The thus obtained crystals showed the same physical data obtained in Inventive Example 3.

Pharmacological test examples of the compound of the present invention are shown in the following, in which the results are obtained mainly using its anhydrate.

With regard to the toxicity, its oral single administration toxicity was 200 mg/kg or more, and serious side effects were not observed in rats by repeated oral administration toxicity test over 10 days and repeated intravenous injection toxicity test over 10 days.

Particularly serious actions upon hemodynamics and electrocardiogram were not observed in dogs, and significant central nervous inhibition actions were not observed in rhesus monkeys even when a dose of 10 mg/kg was administered by intravenous injection.

PHARMACOLOGICAL TEST EXAMPLE 1

Calmodulin inhibition action

The calmodulin inhibition action was evaluated using calmodulin-dependent phosphodiesterase (PDE) inhibition effect as an index. The method of Tompson et al. (*Advances in Cyclic Nucleotide Research* 10, 69, 1979) was modified and used in the test. That is, 50 mM Tris buffer (pH 7.5, containing 5 mM $MgCl_2$ and 1 mg/ml bovine serum albumin), 1 mM $CaCl_2$, [$^3$H]-cGMP, calmodulin (CaM, bovine brain origin), CaM-PDE (calmodulin-dependent phosphodiesterase, bovine brain origin) and a test sample were mixed and incubated at 30° C. for 10 minutes. This was heated for 1 minutes in a boiling water bath to stop the reaction, mixed with snake venom (1 mg/ml) and then allowed to undergo 10 minutes of reaction at 30° C. to effect conversion of 5'-GMP formed by PDE into guanosine. Next, unreacted cGMP was adsorbed to an ion exchange resin (AG1-X8) and then radioactivity in the supernatant fluid obtained by centrifugation was measured using a liquid scintillation counter. The PDE inhibition effect when calculated as $IC_{50}$ value was 5.46 $\mu$M. On the other hand, W-7 used as a control compound showed a value of 33.5 $\mu$M.

PHARMACOLOGICAL TEST EXAMPLE 2

Action upon mouse nitrogen-loaded hypoxia model

This test was carried out in accordance with the method of Albert Wauquier et al. (Japan *J. Pharmacol.*, 38, 1–7 (1985)).

A total of 9 to 10 mice were used in 1 group, and each animal 60 minutes after oral administration of a drug to be tested (30 mg/kg) was put into a transparent container (500 ml capacity) equipped with an air outlet and then the container was fed with nitrogen gas at a rate of 5.0 L/min. The period of time from the commencement of gas feeding until respiratory arrest was measured. When the control group was defined as 100%, the increasing ratio was 15.1%.

PHARMACOLOGICAL TEST EXAMPLE 3

Changes in hippocampus nerve cells in cerebral ischemia model

When transient cerebral ischemia is loaded on a jird, hippocampus nerve cells start to get necrosis several days thereafter, and such a change is called delayed nerve cell death.

The following test was carried out in accordance with the method of T. Kirino (*Brain Res.*, 239, 57–69 (1982)). That is, each jird was loaded with 5 minutes of cerebral ischemia and then sacrificed to count the number of nerve cells remained in the hippocampus CA1 region.

Nerve cells of hippocampus CA1 died out almost completely by the cerebral ischemia, but oral administration of the compound (100 mg/kg) carried out 1 hour after the cerebral ischemia loading showed distinct protecting effect against nerve cell death.

| Test Groups | Hippocampus Nerve Cell Density (cells/mm) |
|---|---|
| Normal group | 194 ± 6.1 |
| Cerebral ischemia group | 9 ± 1.3 |
| Cerebral ischemia + compound group | 131 ± 21.2** |

**: $P < 0.01$ vs. cerebral ischemia group, n = 9–10

PHARMACOLOGICAL TEST EXAMPLE 4

Anti-edema effect in rat microsphere cerebral embolus model

This test was carried out in accordance with the method of Nobutaka Demura et al. (*Neuroscience Res.*, 17, 23–30 (1983)).

Under halothane anesthesia, a Slc;Wis rat (about 300 g) which has been treated with caudal vein cannulation in advance was subjected to neck incision to tear off the left side common carotid artery. Wing process palate artery and external carotid artery on the same side were also torn off and subjected to artery clipping. Carbon microspheres (50±10 $\mu$m in diameter) were suspended in 20% dextran and injected into the left side common carotid artery to effect dispersion of the microspheres in the left cerebral hemisphere via the left internal carotid artery, the common carotid artery was immediately clipped to stop bleeding from the microsphere-injected part, and then the artery clip was removed to restart blood circulation. Thereafter, each drug solution was continuously injected using an infusion pump from the catheter which has been inserted into caudal vein.

Each animal was sacrificed by decapitation 24 hours after the operation, and the brain was excised immediately after the decapitation to measure wet weights of both left and right hemispheres. Each tissue was then dried overnight at 150° C. to measure its dry weight and to calculate water content of each hemisphere.

As a control group, a vehicle group (20% dextran only) was arranged and treated in the same manner.

| Test Groups | Control Side (right hemisphere) | Disease Side (left hemisphere) |
|---|---|---|
| | Water content (%) | |
| Control group (vehicle applied group) | 78.8 ± 0.1 | 81.1 ± 0.3 |
| Compound applied group | | |
| (dose 2 mg/kg/hr, 8 hr) | 78.7 ± 0.1 | 79.8 ± 0.3* |
| (dose 1 mg/kg/hr, 8 hr) | 78.8 ± 0.1 | 80.1 ± 0.4* |

$P < 0.05$ (Students t test) n = 5

INDUSTRIAL APPLICABILITY

3-[2-[4-(3-Chloro-2-methylphenyl)-1-piperazinyl]ethyl]-5,6-dimethoxy-1-(4-imidazolylmethyl)-1H-indazole dihydrochloride 3.5-hydrate was found by the present invention as a novel crystal. This crystal is characterized by its markedly stable storage stability. In consequence, it is useful as a pharmaceutical material.

We claim:

1. A crystal of 3-[2-[4-(3-chloro-2-methylphenyl)-1-piperazinyl]ethyl]-5,6-dimethoxy-1-(4-imidazolylmethyl)-1H-indazole dihydrochloride which substantially has the following X-ray diffraction characteristics

| Lattice spacing d value (Å) | Relative strength |
|---|---|
| 28.1 | medium |
| 27.5 | medium |
| 27.0 | medium |
| 26.4 | medium |
| 25.6 | medium |
| 25.3 | strong |
| 24.7 | medium |
| 24.3 | strong |
| 22.0 | strong |
| 21.4 | weak |
| 20.9 | medium |
| 19.3 | extremely weak |
| 17.8 | medium |
| 15.4 | medium |
| 13.8 | medium |
| 9.60 | extremely strong |
| 9.09 | extremely weak |
| 8.46 | medium |

2. A method for producing 3-[2-[4-(3-chloro-2-methylphenyl)-1-piperazinyl]ethyl]-5,6-dimethoxy-1-(4-imidazolylmethyl)-1H-indazole dihydrochloride substantially having the following X-ray diffraction characteristics

| Lattice spacing d value (Å) | Relative strength |
|---|---|
| 28.1 | medium |
| 27.5 | medium |
| 27.0 | medium |
| 26.4 | medium |
| 25.6 | medium |
| 25.3 | strong |
| 24.7 | medium |
| 24.3 | strong |
| 22.0 | strong |
| 21.4 | weak |
| 20.9 | medium |
| 19.3 | extremely weak |
| 17.8 | medium |
| 15.4 | medium |
| 13.8 | medium |
| 9.60 | extremely strong |
| 9.09 | extremely weak |
| 8.46 | medium | which comprises
  (a) treating free form 3-[2-[4-(3-chloro-2-methylphenyl)-1-piperazinyl]ethyl]-5,6-dimethoxy-1-(4-imidazolylmethyl)-1H-indazole with hydrochloric acid in the presence of water, or
  (b) treating a 3-[2-[4-(3-chloro-2-methylphenyl)-1-piperazinyl]ethyl]-5,6-dimethoxy-1-(4-imidazolylmethyl)-1H-indazole hydrochloride hydrate, which is a hydrate and/or hydrochloride containing less water and/or hydrochloride than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate, with water or/and hydrochloric acid, or
  (c) removing water and/or hydrochloric acid from a (3-[2-[4-(3-chloro-2-methylphenyl)-1-piperazinyl]ethyl]-5, 6-dimethoxy-1-(4-imidazolylmethyl)-1H-indazole hydrochloride hydrate which is a hydrate and/or hydrochloride containing more water and/or hydrochloride than the 3-[2-[4-(3-chloro-2-methylphenyl)-1-piperazinyl]ethyl]-5,6-dimethoxy-1-(4-imidazolylmethyl)-1H-indazole dihydrochloride 3.5-hydrate to be produced, or
  (d) treating a salt of 3-[2-[4-(3-chloro-2-methylphenyl)-1-piperazinyl]ethyl]-5,6-dimethoxy-1-(4-imidazolylmethyl)-1H-indazole other than hydrochloride in the presence of water and hydrochloric acid.

* * * * *